US006931282B2

(12) United States Patent
Esler

(10) Patent No.: US 6,931,282 B2
(45) Date of Patent: Aug. 16, 2005

(54) METHOD TO CREATE PACEMAKER TIMING CYCLES

(75) Inventor: James A. Esler, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 622 days.

(21) Appl. No.: 10/155,908

(22) Filed: May 23, 2002

(65) Prior Publication Data

US 2003/0220671 A1 Nov. 27, 2003

(51) Int. Cl.$^7$ .............................................. A61N 1/362
(52) U.S. Cl. ...................... 607/9; 607/4; 607/5; 607/30
(58) Field of Search ............................ 607/4, 5, 9, 27, 607/30, 32; 600/508–509

(56) References Cited

U.S. PATENT DOCUMENTS 6,112,119 A * 8/2000 Schuelke et al. ............... 607/9
6,400,985 B1 * 6/2002 Amely-Velez .................. 607/9
2003/0056137 A1 * 3/2003 Huelskamp .................. 713/600

* cited by examiner

Primary Examiner—Carl Layno
(74) Attorney, Agent, or Firm—Schwegman, Lundberg, Woessner & Kluth, P.A.

(57) ABSTRACT

A cardiac rhythm management system having a plurality of timers and programming adapted to receive a status array. The status array is based on the status of each timer of the plurality of timers and includes intrinsic activity detection for each pace sense site. The plurality of timers are initiated concurrent with a detected event or condition. The status array is masked according to an enable array and an interrupt signal is generated based on selected bit transitions of the status array. The interrupt signal initiates a predetermined therapy or function based on the status array. A FIFO buffer preserves the order of senses and paces for further processing. The predetermined therapy or function includes determining a mode of operation of the system.

31 Claims, 6 Drawing Sheets

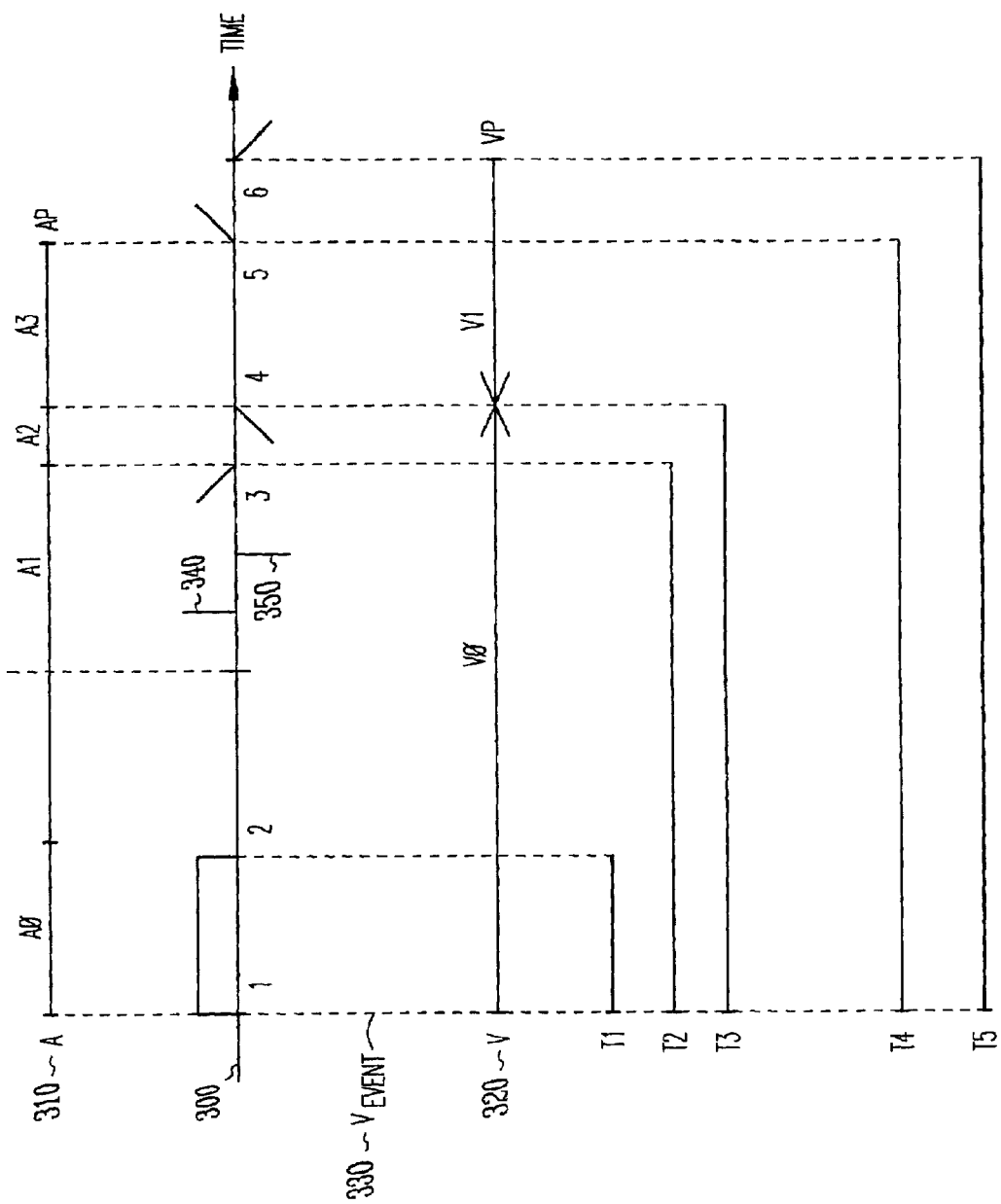

METHOD TO CREATE PACEMAKER TIMING CYCLES

TECHNICAL FIELD

This invention relates generally to cardiac rhythm management systems and particularly, but not by way of limitation, to a method of creating timing cycles.

BACKGROUND

Cardiac rhythm management systems provide heart therapy based on sensed conditions of the heart. Irregular cardiac rhythms, known as cardiac arrhythmia, is one example of a medical condition that may be treated with a cardiac rhythm management system. Cardiac arrhythmia result in diminished blood circulation. Examples of such systems include, among other things, pacemakers or pacers. Pacers deliver timed sequences of low energy electrical stimuli, called pace pulses, to the heart, such as via a transvenous leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem faced by cardiac rhythm management systems is the treatment of congestive heart failure (also referred to as "CHF"). CHF, which can result from long-term hypertension, is a condition in which the walls of at least one side of the heart (e.g., the left side) becomes disproportionately enlarged and the heart muscle associated with the left atrium and ventricle displays less contractility. This decreases cardiac output of blood through the circulatory system which, in turn, may result in an increased heart rate and less resting time between heartbeats. The heart consumes more energy and oxygen, and its condition typically worsens over a period of time.

As one side of the heart (e.g., the left side) becomes disproportionately enlarged, the intrinsic electrical heart signals that control heart rhythm are also affected. In a normal heart, such intrinsic signals originate in the sinoatrial (SA) node in the upper right atrium, traveling through and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through and depolarizes the ventricular heart tissue such that resulting contractions of the right and left ventricles are triggered substantially simultaneously.

Where one side of the heart has become disproportionately enlarged due to congestive heart failure, however, the ventricular intrinsic heart signals may travel through and depolarize the left side of the heart more slowly than in the right side of the heart. As a result, the left and right ventricles do not contract simultaneously, but rather, the left ventricle contracts after the right ventricle. This delay between right ventricular and left ventricular contractions reduces the pumping efficiency of the heart due to movement of the septal wall between right and left sides of the heart. Congestive heart failure may also result in an another symptom, that is, an overly long delay between atrial and ventricular contractions. This too-long delay between atrial and ventricular contractions also reduces the pumping efficiency of the heart.

Historically, most cardiac rhythm management systems have addressed only one or a few heart conditions, such as CHF, bradyarrhythmias or tachyarrhythmias. For example, a device tailored to treat bradyarrhythmias may be incapable of providing therapy for tachyarrhythmias.

Efforts to meet a variety of different design objectives using hardware implemented cardiac rhythm management systems have illuminated several disadvantages. In a hardware implementation, typically a state machine is designed to account for all possible pacing and sensing combinations for all known modes of operation. One disadvantage of a hardware implementation is that the design tolerates little or no changes. Such design brittleness complicates implementation of subsequent design modifications or error corrections. In addition, correct operation of a hardware implementation cannot readily be inexpensively verified.

A purely software implementation is not without problems either. In one embodiment of a software implementation of a cardiac rhythm management system, a single ripple timer is triggered and multiple compare registers are provided to trigger selected functions. The ensuing comparisons are inefficient in that processor capacity is diverted during each comparison. In addition, the processor is forced to complete various calculations to assess the status or progress of the process. This clock rollover problem further taxes processor time and draws power to execute.

What is needed is a system that is flexible to later design changes, yet draws little processing power or time. The system should also allow full testing and evaluation of a wide variety of combinations of pacing and timing events.

SUMMARY

This document discloses, among other things, a cardiac rhythm management system which uses outputs from a plurality of timers and sensors to form a status array that is then masked using an enable array. The resulting array, referred to herein as a masked status array, is mapped to a particular pacemaker mode and also allows for identifying which therapy functions are to be executed by the system. The individual digital bits of the status array are determined by the status of individual timers and sensors coupled to the heart. A FIFO (first in first out) buffer preserves the temporal relationship between timer events and sensed events.

One embodiment of the present system strikes a balance between hardware and software that preserves extensibility, reduces the design brittleness of a hardware intense approach and reduces processor load of a software-intense approach.

One aspect of the present system includes a method including starting one or more timers upon detecting a first cardiac event, monitoring for senses upon detecting the first cardiac event and storing a status array having a plurality of status bits. Each bit in the status array corresponds to either a timer or sense circuit. Timer status refers to states in the pacemaker engine. The method also includes executing a particular function selected from a plurality of functions based on a logical AND of the status array with an enable array.

In one embodiment, the system includes a sense circuit adapted to sense heart signals from a heart, a plurality of timers that are coupled to the sense circuit, with each timer initiated substantially simultaneously. The system also includes a therapy circuit adapted to deliver therapy to one or more chambers of the heart and a processor coupled to the sense circuit and the timers and adapted to control the therapy circuit based on a status array derived from a status signal from each timer. In one embodiment, the processor includes a microprocessor. In one embodiment, the present subject matter includes computer readable, or implemented, instructions adapted to perform the methods described herein.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

FIG. 3 illustrates generally one possible series of event markers occurring over a period of time.

DETAILED DESCRIPTION

Figure 1:
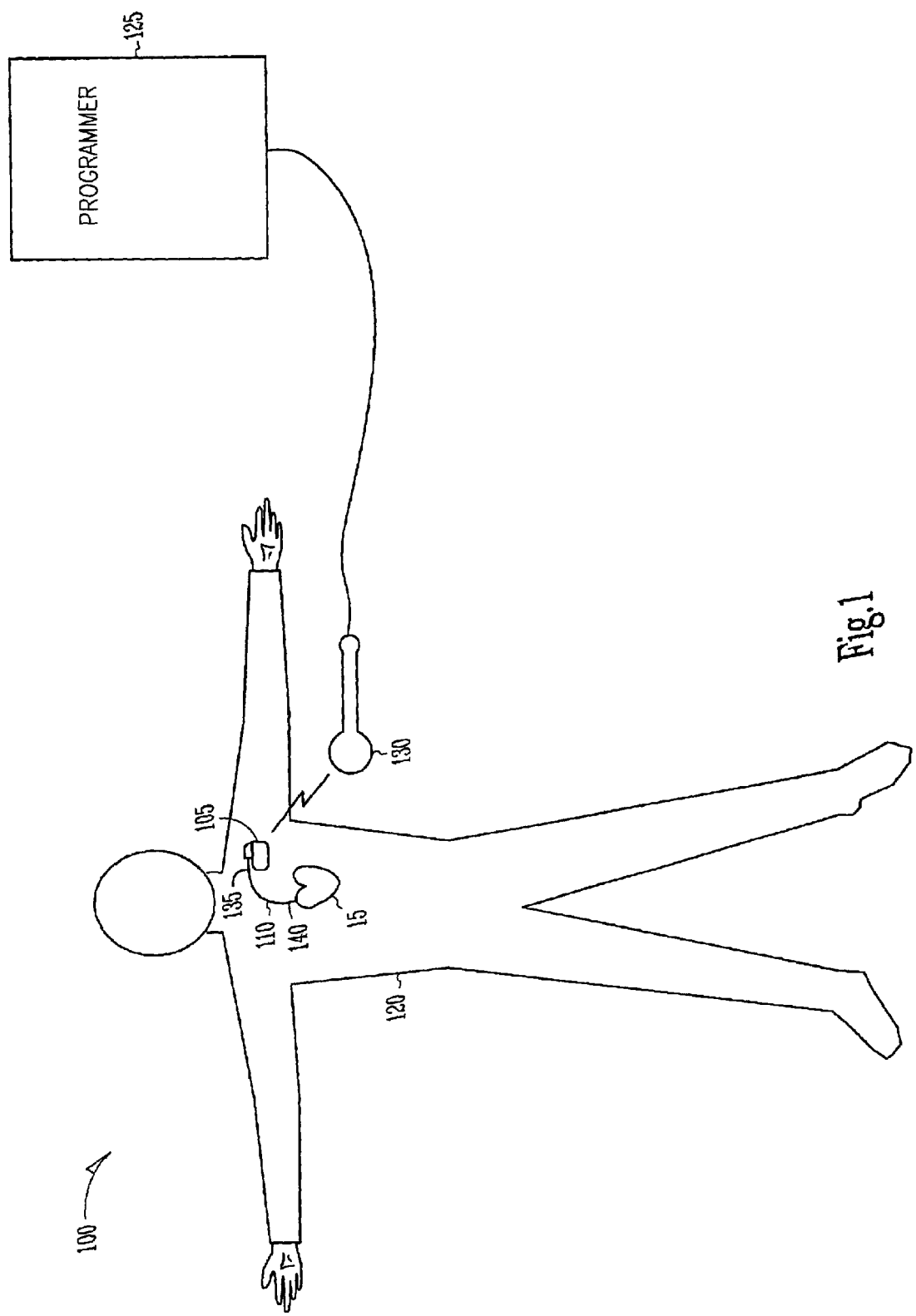
FIG. 1 is a schematic drawing illustrating one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

FIG. 1 includes a schematic drawing illustrating, by way of example, but not by way of limitation, one embodiment of portions of a cardiac rhythm management system 100 and an environment in which it is used. In FIG. 1, system 100 includes implantable cardiac rhythm management device 105, also referred to as an electronics unit, which is coupled by intravascular endocardial lead 110, or other lead, to heart 15 of patient 120. In one embodiment, system 100 is coupled to heart 15 by an epicardial lead (not shown). System 100 also includes external or other remote programmer 125 providing wireless communication with device 105 using telemetry device 130. Catheter lead 110 includes proximal end 135, which is coupled to device 105, and distal end 140, which is coupled to one or more portions of heart 15.

Figure 2:
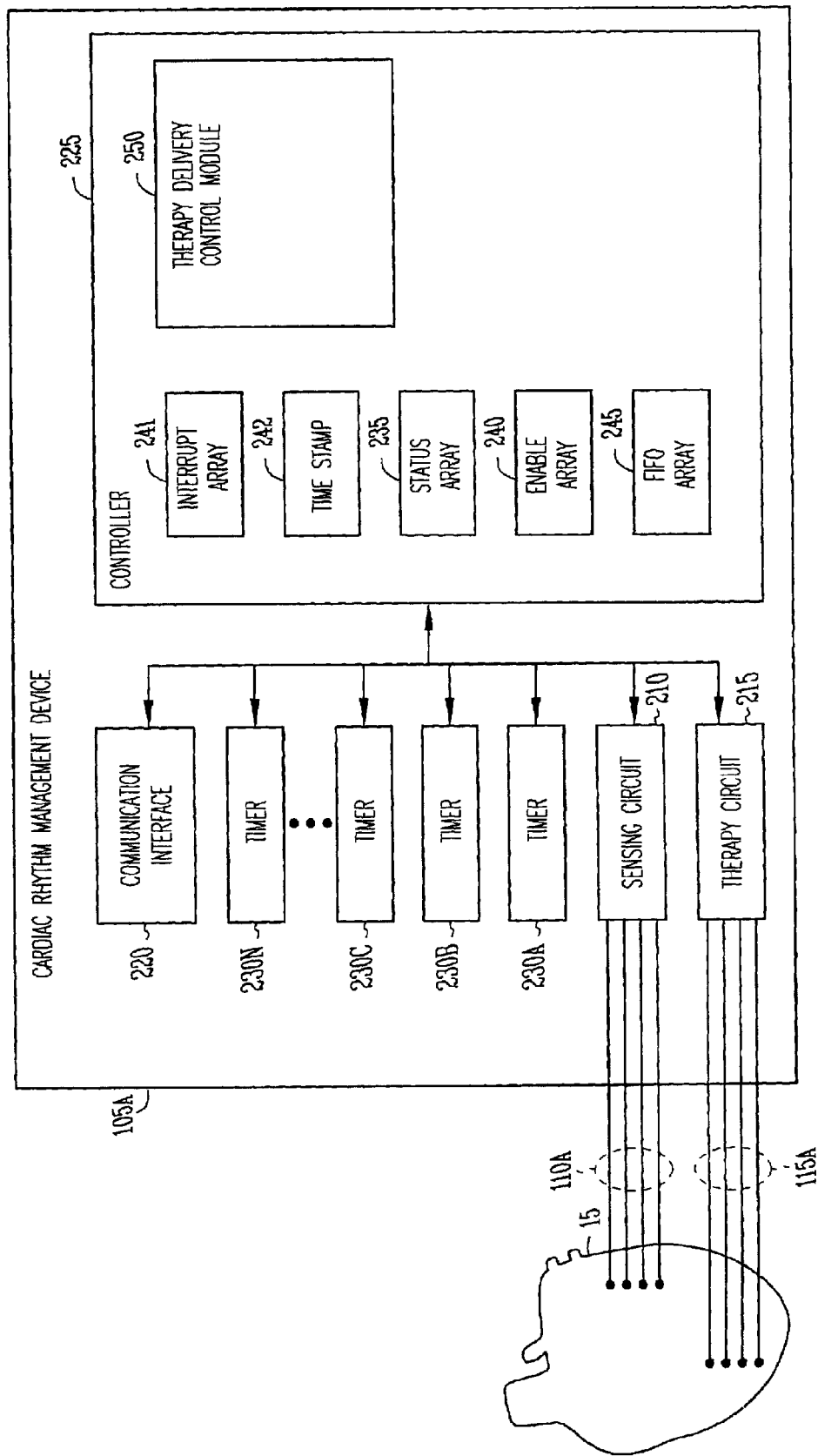
FIG. 2 is a schematic drawing illustrating generally one embodiment of portions of a cardiac rhythm management device coupled by leads to a heart.

FIG. 2 is a schematic drawing illustrating generally, by way of example, but not by way of limitation, one embodiment of portions of cardiac rhythm management device 105A coupled by leads 110A and 115A to heart 15. In this embodiment, lead 110A includes one or more electrodes (electrical contacts) disposed in, around, or near a portion of heart 15, such as one or more of a ring, tip, coil, or other electrode, for sensing signals or delivering one or more of pacing, defibrillation, countershock, cardioversion, or anti-tachyarrhythmia pacing (ATP) therapy to heart 15.

In FIG. 2, lead 115A includes one or more electrodes disposed in, around, or near a portion of heart 15, such as one or more of a ring, tip, coil or other electrode, for sensing signals or delivering one or more of pacing, defibrillation countershock, cardioversion, or anti-tachyarrhythmia pacing therapy to heart 15.

Device 105A includes components that are enclosed in a hermetically-sealed can. Additional electrodes may be located on the can, or on an insulating header, or on other portions of device 105A, for providing one or more of unipolar or bipolar pacing or defibrillation energy in conjunction with the electrodes disposed on or around heart 15. Other forms of electrodes include meshes, patches, and screw-in tips which may be applied to endocardial or epicardial portions of heart 15 or which may be implanted in other areas of the body to help "steer" multi-phasic or direct current electrical currents produced by device 105A. The present method and apparatus will work in a variety of configurations and with a variety of electrical contacts or electrodes.

In one embodiment of the present system, one or more conductors of lead 110A is electrically coupled to one or more conductors of lead 115A, such that electrodes associated with different regions of the heart share common sensing circuits 210 and common therapy circuits 215. Variations of the single-channel embodiment include other channels (e.g., associated with other heart chambers or multiple pacing sites within a chamber), but at least one of the channels is coupled to electrodes at two different locations, such as within a single chamber or within two different chambers of heart 15. In one example, leads 110A and 115A are implemented as a single lead that is bifurcated to allow disposition of electrodes at different locations, such as associated with two different chambers of heart 15. Electrodes may be positioned in different chambers or at different locations within a single chamber. In the figure, leads 110A and 115A are each terminated with four electrodes within heart 15. In another example, leads 110A and 115A are separate leads that are received at receptacles at a header portion of device 105A. In one embodiment, at least one conductor of lead 110A is electrically coupled to at least one conductor of lead 115A within the header or elsewhere in device 105A, or using an adapter. In one embodiment, lead 110A is an intravascular endocardial lead with an electrode disposed near the apex of right ventricle of heart 15, and lead 115A is an epicardial lead with a screw-in or other electrode associated with left ventricle of heart 15. In another embodiment, lead 115A is an intravascular endocardial lead introduced into coronary sinus of heart 15. In one embodiment, lead 115A extends into the great cardiac vein such that an intravascular electrode is associated with tissue of the left ventricle of heart 15.

In FIG. 2, device 105A also includes a communication interface 220, such as a circuit for communicating with remote programmer 125 via telemetry device 130. In one embodiment, communication interface includes a near field telemetry system or inductive coupling.

Controller 225 communicates one or more signals with one or more timers. In the figure, exemplary timers are illustrated as timer 230A, timer 230B, timer 230C and timer 230N, however, there may be any number of timers within a particular device 105A and in communication with controller 225. In one embodiment, each timer is implemented in hardware and at least one timer includes a ripple counter having 16 bits of data. Each timer may be running or not running and the status of the timer is represented by a single logical level. A data bit corresponding to the logical level of the output of each timer is stored in a predetermined place within multi-bit status array 235. Each timer provides a single bit to the status array.

Sensing circuit 210 receives intrinsic heart signals from leads 110A and 115A. The output of sensing circuit 210 is mapped to a logical "1" or logical "0" level and is stored in status array 235.

Controller 225 includes one or more of hardware modules, software modules, firmware modules, or other components or executable instructions. FIG. 2 illustrates, in modular block form, interrupt array 241, time stamp 242, status array 235, enable array 240, FIFO buffer 245, and therapy delivery control module 250. Some of the various modular blocks are understood to include one or more sequences of steps carried out on controller 225, such as by executing stored microcode or other instructions. Interrupt array 241 includes programmable data registers corresponding to events that call for further processing. For example, under certain circumstances, a sensed atrial event occurring during a post ventricular atrial refractory period (PVARP) is ignored and under other circumstances, the same event would trigger the processor to perform a particular routine. Time stamp 242 provides data corresponding to the time at which a selected event has occurred. Status array 235 includes a multi-bit register with the value of each bit provided by a corresponding sensing circuit or timer. Enable array 240 includes a register having stored therein a digital value corresponding to a masking function. In one embodiment, enable array 240 refers to a memory having contents determined by controller 225 or programmer 125.

Controller 225 receives one or more signals from sensing circuit 210 that include information about sensed cardiac events. Based on sensed events, among other things, portions of an algorithm executed by controller 225 determines timing of pacing, defibrillation, or other therapy, and also determines other therapy parameters. Accordingly, controller 225 provides control signals to therapy circuit 215 for controlling the delivery of output energy or other therapy to heart 15. Such therapy includes, for example, pacing energy pulses delivered simultaneously to right and left ventricles of heart 15. In another example, such therapy includes cardioversion/defibrillation/countershock energy pulses delivered simultaneously to right and left ventricles of heart 15.

The following is a description of a representative timer, such as, for example, timer 230A. Timer 230A includes an input and an output coupled to controller 225. Timer 230A begins running upon receiving a trigger signal. In various embodiments, the trigger signal is generated based on a signal received from sensing circuit 210, therapy circuit 215, controller 225, programmer 125 or other triggering source. The output of timer 230A is a binary signal indicating the status of the timer. In one embodiment, the output is a logical "1" during the predetermined period of time when timer 230A is running and a logical "0" when not running.

In one embodiment, one or more timers initiate an autonomous function upon expiration of the programmed time period. For example, each of four dedicated timers may be coupled to each of four different chambers of the heart, namely right atrial (RA), left atrial (LA), right ventricle (RV) and left ventricle (LV). As another example, each of four dedicated timers may all be located in the same chamber of the heart. The four dedicated timers are referred to herein as escape timers. More or less than four dedicated timers may be used. At the conclusion of the time period of each respective escape timer, an electrical pulse is delivered to that chamber of the heart. For example, when the period timed by the RA escape timer has lapsed, the device automatically, and immediately, delivers an electrical pulse to the RA.

In one embodiment, one or more timers initiate an interrupt, or wake-up sequence, at controller 225 after the timed period has lapsed. The interrupt signal is received by the controller and may trigger execution of a subsequent process.

In one embodiment, one or more timers provide status information that is outcome determinative. In particular, the output of such a timer determines a mode of pacing or function to be executed by controller 225. In other embodiments, the output of a particular timer is not determinative but is helpful for establishing the context of later functions. For such timers, the fact that the time period has expired, or not expired, is stored in a memory accessible to controller 225 and may or may not be used for subsequent processing.

The output of controller 225 provides a signal to therapy delivery control module 250. Therapy delivery control module 250 executes a therapy delivery algorithm for determining the timing and other parameters of pacing therapy, anti-tachyarrhythmia therapy such as defibrillation countershocks or anti-tachyarrhythmia pacing (ATP), or other therapy. Module 250, may include hardware or software, and provides a signal to therapy circuit 215 which delivers an electrical stimulus to heart 15 via lead 115A.

Tables 1 and 2 provide exemplary data for one particular exemplary embodiment of the present subject matter. Other data, structures or software may also be used without departing from the present subject matter. The identity of several individual timers and sensors appears in column 1 of Table 1. Any number of timers may be included, however, the embodiment shown identifies Timer 0, Timer 1, Timer 2 and Timer N. The column also includes four escape timers associated with each of four different chambers of the heart. The escape timers provide an immediate pacing signal upon expiration of the timed period. Each timer in column 1 has a predetermined duration. The time period associated with each timer is programmable using controller 225 and in one embodiment, programmable using programmer 125. Column 1 also includes four sense detect signals with one each associated with each of the chambers of the heart. Each of the timers and sense detectors enumerated in column 1 provides a binary output signal corresponding to the state of the sense or timers.

Column 2 illustrates an exemplary status array derived from the signals received from each of the entries in column 1. For example, at the particular point in time depicted, Timer 0 has provided a logical "0" which may denote that Timer 0 has expired. In another embodiment, a logical "0" may denote that Timer 0 continues to run. Also in column 2, Escape Timer RA indicates a logical "1" which indicates, according to one embodiment, that an escape beat has been delivered to the heart. Each of the Sense Detects indicates a logical "1" denoting, according to one embodiment, that each has sensed a predetermined signal in the heart.

Column 3 illustrates an exemplary enable array. In various embodiments, the enable array is received from programmer 125, stored in a memory register accessible to controller 225 or generated dynamically by controller 225. The contents of the enable array are programmable, thus eliminating the need for surgical reimplantation to effectuate programming changes.

Column 4 illustrates the results of a logical AND operation using the status array of column 2 and the enable array of column 3. In one embodiment, the contents of column 4 determines the pacing mode and the function to be executed by device 105. The pacing mode and function to be executed are programmable (or reprogrammable), thus eliminating the need for surgical reimplantation to effectuate programming changes.

Column 5 illustrates data in an interrupt array. In one embodiment, the data in the interrupt array is programmable. The table illustrates a representative interrupt array. For those rows having a logical 1 in the interrupt array, upon expiration of a timer or sensing of an event, a particular function is performed by the processor, and for those rows having a logical 0, the timer or event is ignored.

Column 6 of Table 1 indicates the contents of a FIFO with time stamp and each cell is marked with a rightward pointing arrow. The arrows in column 6 indicate that the data from columns 2, 3, 4 and 5 are sequentially shifting rightward with passing time. For example, in one embodiment, data from column 5 at a first time is shifted into column 6 at a second, later, time.

TABLE 1

| Column 1 Individual Timer/Detect | Column 2 Individual Timer/Detect Status Array | Column 3 Enable Array | Column 4 (Status Array) AND (Enable Array) | Column 5 Interrupt Array | Column 6 FIFO with time stamp |
|---|---|---|---|---|---|
| Timer 0 | 0 | 0 | 0 | 0 | → |
| Timer 1 | 0 | 0 | 0 | 0 | → |
| Timer 2 | 1 | 1 | 1 | 1 | → |
| Timer 3 | 0 | 1 | 0 | 1 | → |
| Timer N | 1 | 0 | 0 | 1 | → |
| Escape Timer RA | 1 | 1 | 1 | 0 | → |
| Escape Timer RV | 1 | 1 | 1 | 1 | → |
| Escape Timer LA | 0 | 1 | 0 | 0 | → |
| Escape Timer LV | 0 | 1 | 0 | 0 | → |
| RA Sense Detect | 1 | 1 | 1 | 1 | → |
| RV Sense Detect | 1 | 1 | 1 | 1 | → |
| LA Sense Detect | 1 | 0 | 0 | 0 | → |
| LV Sense Detect | 1 | 0 | 0 | 0 | → |

Table 2 below illustrates exemplary pacing modes and functions based on the data derived from Table 1. For example, in row 1, the table shows that with a particular bit pattern resulting from the masking operation of the enable array with the status array, the mode of the device is DDD. DDD, appearing in rows 1 through 4, refers to a pacing mode that senses and stimulates both atrium and ventricle and where the stimulation rate is determined by the maximum tracking rate and a minimum rate. VDD, appearing in rows 5 through 8, refers to a pacing mode that senses the atrium and ventricle and paces the ventricle. DDI, appearing in rows 9 through 12, refers to a pacing mode that senses and stimulates both atrium and ventricle and where the stimulation rate is fixed. VVI, appearing in rows 13–16, refers to a pacing mode that stimulates and senses the ventricle at one rate. XYZ, appearing in rows 17 through 20, refers to any of a number of other pacing modes.

Referring again to the example in row 1, the combination of the status array and the enable array yields case 1, resulting in the execution of group 1 DDD functions. The functions defined by "group 1 DDD" are programmable in software executing on controller 225. The functions may include treating a particular event occurring at one point in time as having occurred at another point in time. The functions may include delivering therapy according to a predetermined schedule. The functions may include storing in memory, the events during a particular time period. Other functions, or any number of functions, may also be performed and the foregoing is merely illustrative.

Referring to row 7, the combination yields case 3, group 3 VDD functions. Here, the functions may include resetting a particular memory register based on data sensed at a predetermined portion of the heart. The functions may also include setting a register to control subsequent functions. The functions may include looping algorithms that interact with prior or later functions that may have been, or will be, performed by device 105.

Other functions are also contemplated. It will be appreciated that there may zero, one, or more functions associated with any particular mode and case.

The information presented in Table 2 may be encoded in software using a variety of techniques, including for example, a look-up table or by means of a series of questions branching to a particular result.

TABLE 2

| Row | Mode | Case | Results |
|---|---|---|---|
| 1 | DDD | case 1 | execute group 1 DDD functions |
| 2 | DDD | case 2 | execute group 2 DDD functions |
| 3 | DDD | case 3 | execute group 3 DDD functions |
| 4 | DDD | case N | execute group N DDD functions |
| 5 | VDD | case 1 | execute group 1 VDD functions |
| 6 | VDD | case 2 | execute group 2 VDD functions |
| 7 | VDD | case 3 | execute group 3 VDD functions |
| 8 | VDD | case N | execute group N VDD functions |
| 9 | DDI | case 1 | execute group 1 DDI functions |
| 10 | DDI | case 2 | execute group 2 DDI functions |
| 11 | DDI | case 3 | execute group 3 DDI functions |
| 12 | DDI | case N | execute group N DDI functions |
| 13 | VV1 | case 1 | execute group 1 VV1 functions |
| 14 | VV1 | case 2 | execute group 2 VV1 functions |
| 15 | VV1 | case 3 | execute group 3 VV1 functions |
| 16 | VV1 | case N | execute group N VV1 functions |
| 17 | XYZ | case 1 | execute group 1 XYZ functions |
| 18 | XYZ | case 2 | execute group 2 XYZ functions |
| 19 | XYZ | case 3 | execute group 3 XYZ functions |
| 20 | XYZ | case N | execute group N XYZ functions |

The status array is based on the status of each timer of the plurality of timers and is based on intrinsic activity detected at each pace sense site. The plurality of timers are initiated concurrent with a detected event or condition. The status array is masked according to an enable array and an interrupt signal is generated based on selected bit transitions of the status array. The interrupt signal initiates a predetermined therapy or function based on the status array. A FIFO buffer preserves the order of events (including, for example, senses and paces) for further processing. The predetermined therapy or function includes determining a mode of operation of the system.

FIG. 3 illustrates generally, by way of example, but not by way of limitation, a possible series of event markers occurring over a period of time. In the figure, the markers illustrate an example of the occurrence of one possible set of events during a single cycle of a DDD mode pacing event. Other pacing modes are also contemplated, including, for example, VVV mode.

With reference to FIG. 3, time line 300 includes points 1, 2, 3, 4, 5 and 6 and denotes later time in the rightward direction. Events above time line 300 occur in the atrium and those immediately below occur in the ventricle. For example, line 340 depicts an atrial event and line 350 depicts a ventricular event. According to the embodiment shown, an event occurring in the atrium during time A0 is ignored for having occurred too soon after a ventricular event. In the illustration, the ventricular event occurred at point 1 on time line 300.

In addition, an atrial event occurring during A1 is treated as though it occurred at point 3, which coincides with the beginning of period A2. This figure demonstrates an example of modeling the behavior of the cardiac rhythm management system.

The time between point 3 and point 4 represents an AV delay period and allows time during with the ventricle fills with blood after the atrium has contracted.

At time 330 (point 1), the ventricle event has triggered the starting of a plurality of timers, illustrated in the lower portion of the figure as T1, T2, T3, T4 and T5. Timer T1 runs from point 1 to point 2 and represents, in one embodiment, the PVARP during which the atrium is non-responsive to electrical stimuli. Timer T2 runs from point 1 to point 3, and represents, in one embodiment, an atrial fast smoothing function. Timer T3 runs from point 1 to point 4, and represents, in one embodiment, a ventricular fast smoothing function. Timer T4 runs from point 1 to point 5 and represents, in one embodiment, an AP (atrial pace) timer and timer T5 runs from point 1 to point 6, and represents, in one embodiment, a VP (ventricular pace) timer. At point 6, the timers are all restarted.

The use of the timers and sense signals efficiently provides information to the controller to determine the status of the timed events.

The timers in the present subject matter may operate at any particular clock frequency. In one embodiment, the timer intervals are between 1 and 8 milliseconds in duration, however, the clock may operate at any frequency.

The pattern of events illustrated in FIG. 3 can occur repeatedly.

Figure 4A:
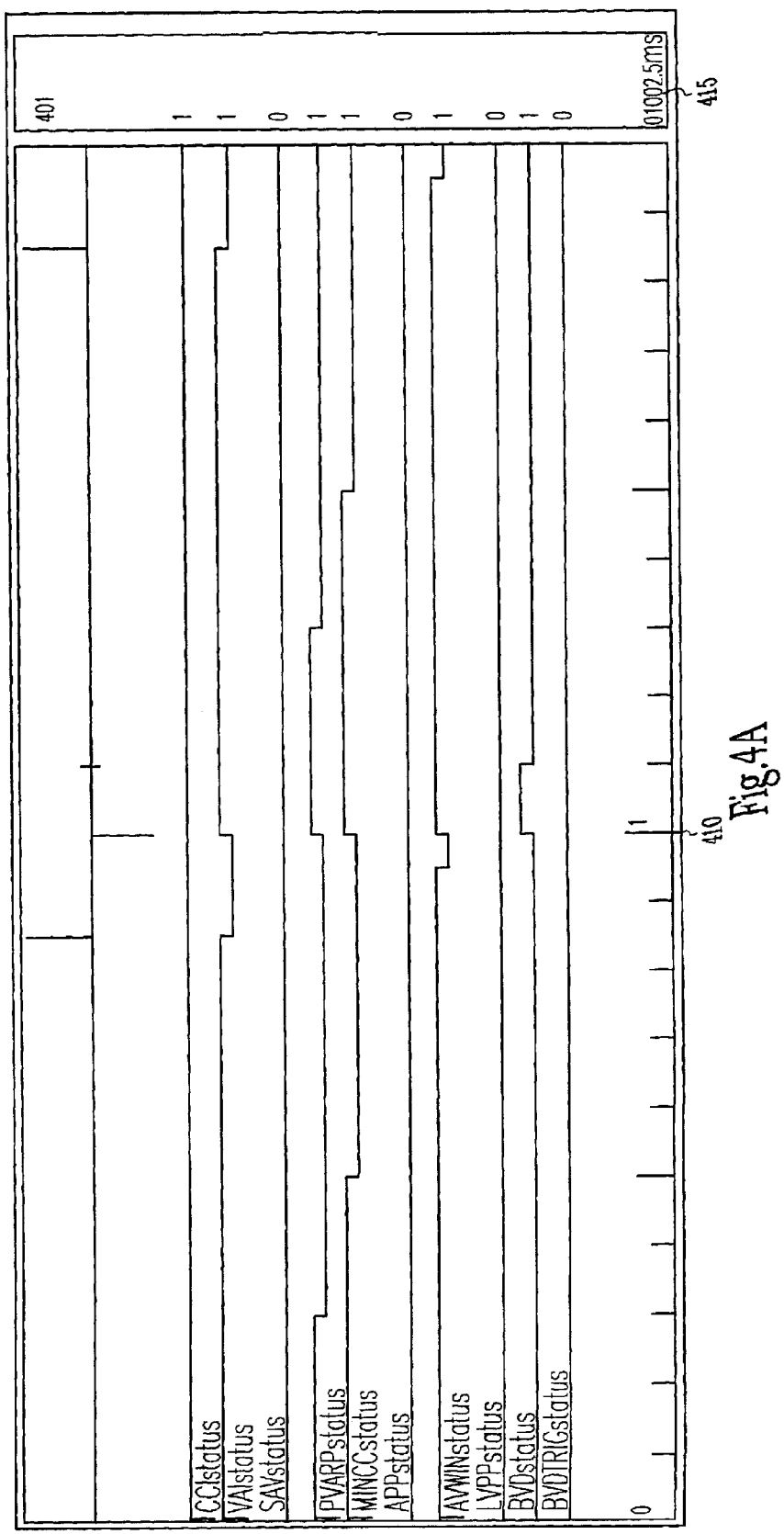
FIG. 4A includes a state diagram illustrating generally one technique of generating pacemaking cycles based on a status array.

FIG. 4A includes a state diagram illustrating generally, by way of example, but not by way of limitation, a screen shot view of a set of timers according to one embodiment. The figure also illustrates values in a status array based on an instant in time of the state diagram.

Timers illustrated in the figure include those labeled as CCIstatus, VAIstatus, SAVstatus, PVARPstatus, MINCCstatus. In one embodiment, the PVARPstatus timer is adapted to time the period of time following a ventricular sense or pace while atrial senses are ignored. The MINCCstatus timer is adapted to time the period of time following a ventricular sense or pace until the point where an atrial sense is allowed to be used to trigger the starting of the SAVstatus. In one embodiment, the SAVstatus timer is adapted to time the period of time following an atrial sense until when the ventricle is paced, baring an intervening ventricle sense. In one embodiment, the VAIstatus timer is adapted to time the period of time following a ventricular sense or pace until the atrium is paced, baring an intervening atrial or ventricular sense. In addition, in one embodiment, a CCIstatus timer is adapted to time the period of time of the lower rate limit (that is, the slowest ventricular paced rate allowed). In addition other timers are also contemplated, including, for example, those that may be associated with CHF, such as, APPstatus (atrial pacing preference status), LVPPstatus (left ventricular pacing protection status), BVDstatus (bi-ventricular delay status) and BVDTRIGstatus (bi-ventricular delay trigger status).

The foregoing timers are illustrative and not to be construed as limiting. Timers can be assigned to time various events or durations. For example, timers may be programmed to monitor minimum and maximum escape times. In one embodiment, a timer is assigned to monitor refractory times or PVARP times. In one embodiment, a timer is assigned to clock rate smoothing windows with each window having a minimum and maximum rate in a selected chamber of the heart. Suitable programming executing on controller 225 allows the assignments of each timer to be changed. For example, a timer initially assigned to monitor PVARP times may later be assigned to monitor a particular refractory time in another portion of the heart. In one embodiment, a timer is assigned to a particular function by suitable programming.

At time 410 on the horizontal axis, the status value of each timer is captured in the status array shown at 415. Here, the status array indicates a value of 1101101010, indicating that some timers remain running and others have expired.

Controller 225, after having masked the status array contents, provides therapy using therapy delivery control module 250, which executes a therapy delivery algorithm. In one embodiment, the therapy delivery algorithm delivers some form of cardiac therapy.

Figure 4B:
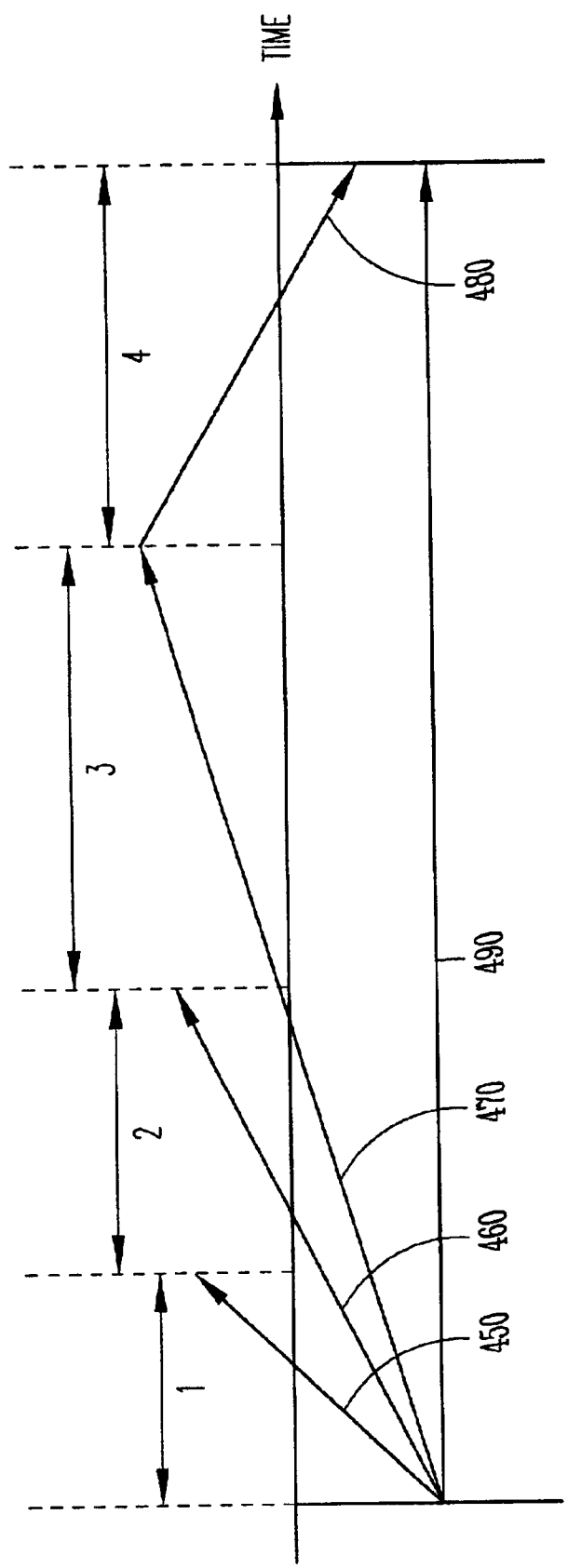
FIG. 4B illustrates generally one possible series of event markers occurring over a period of time.

FIG. 4B illustrates generally one possible series of event markers occurring over a period of time according to one embodiment. Assuming time period 1 corresponds to a PVARP period, then arrow 450 represents a period of time monitored by timer PVARPstatus. During the PVARP period, atrial events are ignored. Time period 2 corresponds to a minimum cardiac cycle time period, and as shown by arrow 460, is monitored by timer MINCCstatus. Time period 3 corresponds to arrow 470, herein denoted VAIstatus. If no atrial event is sensed during time period 3, then the pacemaker issues an atrial pace at the end of period 3. Time period 4 corresponds to a sensed atrial event and is monitored by SAVstatus timer 480. During time period 5, no ventricular events are sensed and the CCIstatus time period is monitored by a timer denoted by arrow 490.

Figure 5:
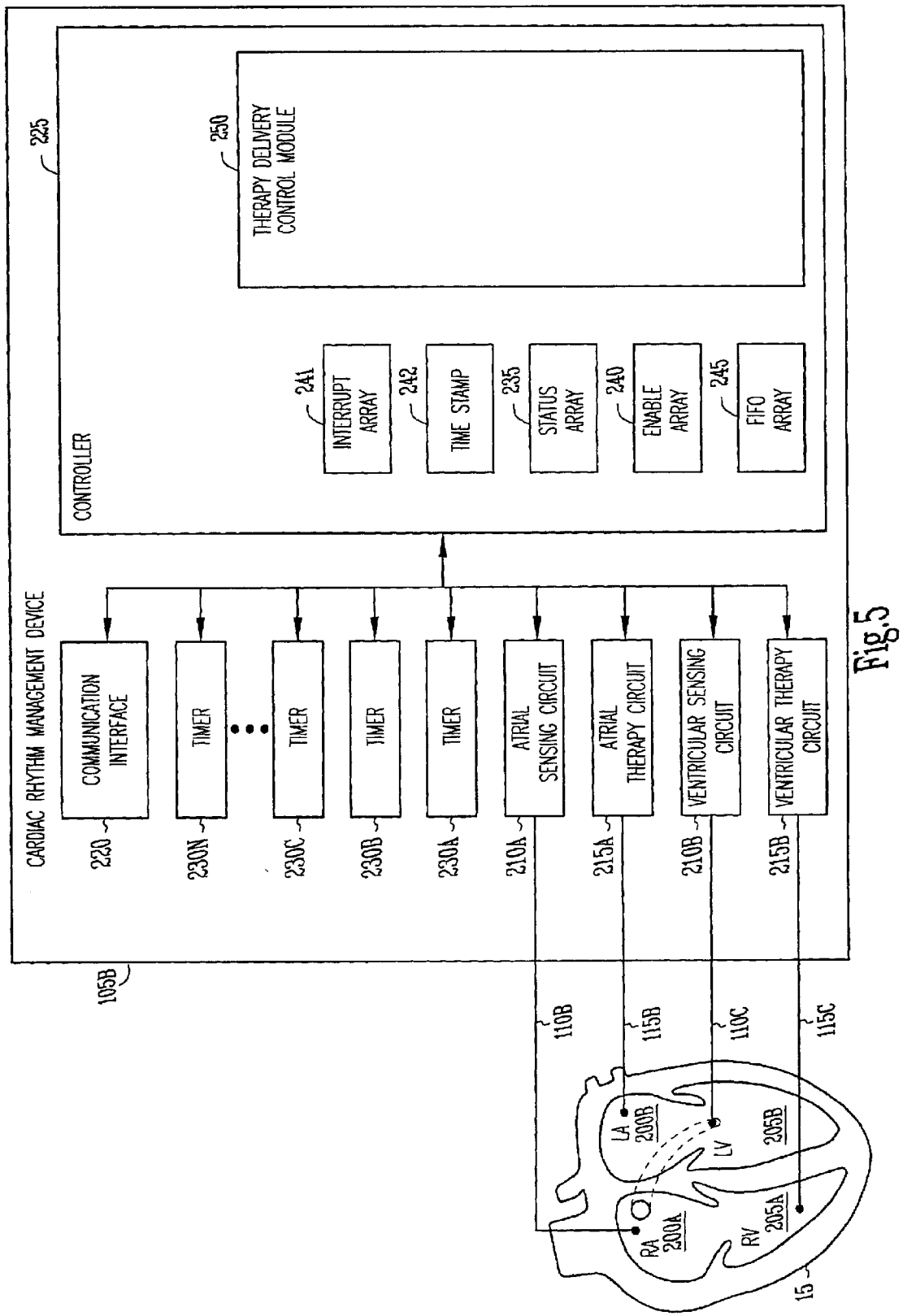
FIG. 5 is a schematic drawing illustrating generally an embodiment of portions of a cardiac rhythm management device coupled by leads to atrial and ventricular chambers of a heart.

FIG. 5 is a schematic drawing illustrating generally, by way of example, but not by way of limitation, an embodiment of portions of device 105B including atrial sensing circuit 210A coupled by lead 110B to right atrium 200A of heart 15 and atrial therapy circuit 215A coupled by lead 115B to left atrium 200B for sensing signals or delivering stimulations or countershocks. Ventricular sensing circuit 210B is coupled by lead 110C to left ventricular 205B of heart 15 and ventricular therapy circuit 215B is coupled by lead 115C to right ventricular 205A for sensing signals or delivering stimulations or countershocks. A plurality of timers, herein denoted as 230A, 230B, 230C and 230N provide timing information relative to the sensed signals from heart 15. Controller 225 and communication interface 220 were discussed above.

Each of timers 230A through 230N are started with a particular event, which, in one embodiment, is a ventricular event. Sense circuits coupled to controller 225, as well as timers 230A through 230N provides status signals for the status array.

The figure illustrates that multiple sensing and therapy may be provided using the present system. In addition, it is to be noted that one or more sensing circuits or one or more therapy circuits may be coupled to a single chamber or portion of a heart.

Alternative Embodiments

Variations of the above embodiments are also contemplated. For example, in one embodiment, the status array is compressed where not all sensing circuits or timers contribute outcome determinative data. In such a case, those non-determinative data bits of the status array are unused. In this context, compression refers to reducing the size of the status array by eliminating the unused bits. For example, in an embodiment having five timers, (namely 230A, 230B, 230C, 230D and 230E) and three sensing circuits, (namely 210A, 210B, 210C), it may be found that timer 230D and sensing circuit 210B provide no information capable of changing the pacing mode or functions executed. In such a case, the status array may be compressed to include data from timers 230A, 230B, 230C and 230E and sensing circuits 210A and 210C and omit data from timer 230D and sensing circuit 210B.

In various embodiments, the enable array is programmed with a particular bit pattern at the time of manufacture or implantation. In one embodiment, controller 225 dynamically determines the contents of the enable array based on instructions executing on controller 225. In one embodiment, the contents of enable array 240 are alterable using programmer 125 coupled to wand 130. In addition, programmer 125 may interrogate device 105 and receive a signal corresponding to the instantaneous contents of interrupt array 241, time stamp 242, status array 235, enable array 240 or FIFO buffer 245. Furthermore, programmer 125 may communicate instructions to device 105 to program a particular bit pattern into interrupt array 241, status array 235, enable array 240 or FIFO buffer 245.

In one embodiment, status array 235 and enable array 240 determine the outcome without need for FIFO buffer 245. In some particular applications, FIFO buffer 245 provides temporal information that does not affect the pacing mode or subsequent functions executed by controller 225.

The present subject matter allows tailoring of the pacing mode and subsequent therapy based on parameters supplied by one or more timers and one or more sensing circuits. For example, the ability to mask a particular timer status or sensing signal effectively allows the system programmer to establish refractory periods on an as needed basis. The combination of enable array 240 and instructions executing on controller 225 can be configured to selectively nullify a sensed signal or a timer status signal.

The present subject matter can be configured to sense, time and pace one or more signals in any of one or more heart chambers. For example, each of four escape timers may be dedicated to each of the four chambers of the human heart, or any two, three or all four may be distributed within a single chamber or region of the heart.

In one embodiment, a logical AND operation is performed using the contents of status array 235 and enable array 240. Other logical operations or sequences of operations may be executed using status array 235 and enable array 240. For example, in various embodiments, a logical OR, NOR, XOR, NAND or any combination of logical operations may be performed.

The status array may also include data not derived from timers or sensing circuits. In one embodiment, status array 235 includes one or more bits based on an internal function of device 105A. For example, where adequate rhythm therapy may be delivered by either of two alternative protocols, a decision as to which to choose may be made based on the charge condition of the battery. Other non-cardiac parameters are also contemplated for inclusion in status array 235.

CONCLUSION

The systems and methods disclosed in this document improves the development, testing, and manufacturing of cardiac rhythm management systems. As a result, the present cardiac rhythm management system can provide therapy to the patient based on sensed events and timers with greater efficiency.

The above description is intended to be illustrative, and not restrictive. Many other embodiments will be apparent to those of skill in the art upon reviewing the above description.

What is claimed is:

1. A method comprising:

starting one or more timers upon detecting a first cardiac event;

monitoring one or more senses upon detecting the first cardiac event;

storing a status array having a plurality of status bits with each one of the one or more timers and each one of the one or more senses represented by a status bit; and executing a particular function selected from a plurality of functions, the particular function selected based on a logical AND of the status array with an enable array.

2. The method of claim 1 further comprising executing computer readable instructions to perform the starting, monitoring, storing and executing the particular function.

3. The method of claim 1 further comprising receiving the enable array.

4. The method of claim 1 further comprising receiving the enable array via a radio frequency (RF) link.

5. The method of claim 1 further comprising storing the enable array in a memory under microprocessor control.

6. The method of claim 1 wherein starting a plurality of timers includes starting one or more escape timers.

7. The method of claim 1 wherein starting a plurality of timers includes starting a first escape timer, starting a second escape timer, starting a third escape timer and starting a fourth escape timer.

8. The method of claim 1 wherein starting a plurality of timers includes starting a right atrial escape timer, starting a right ventricle escape timer, starting a left atrial escape timer and starting a left ventricle escape timer.

9. The method of claim 1 wherein monitoring one or more senses includes receiving one or more intrinsic cardiac activity detection signals.

10. The method of claim 1 further comprising storing the status array in a buffer.

11. The method of claim 1 further comprising storing the status array in a first in first out (FIFO) buffer.

12. The method of claim 1 further comprising storing timer status in a buffer.

13. The method of claim 1 further comprising generating an interrupt signal upon detecting a particular status of a particular bit in the status array.

14. The method of claim 1 further comprising generating an event code based on filtering the status array.

15. A system comprising:
   a sense circuit adapted to sense heart signals from a heart;
   a plurality of timers coupled to the sense circuit, each timer of the plurality of timers initiated substantially simultaneously;
   a therapy circuit adapted to deliver therapy to one or more chambers of the heart; and
   a processor coupled to the sense circuit and coupled to the plurality of timers and adapted to control the therapy circuit based on a status array derived from a status signal from each timer of the plurality of timers.

16. The system of claim 15 wherein the sense circuit is adapted to sense a heart signal from one or more chambers of the heart.

17. The system of claim 15 wherein the plurality of timers includes a plurality of escape timers.

18. The system of claim 15 wherein the plurality of timers includes a right atrial escape timer, a right ventricle escape timer, a left atrial escape timer and a left ventricle escape timer.

19. The system of claim 15 wherein the sense circuit includes a plurality of leads.

20. The system of claim 15 wherein a timer of the plurality of timers includes a ripple counter.

21. The system of claim 15 further comprising one or more intrinsic activity detectors coupled to the sense circuit and wherein the status array is derived from each of the one or more intrinsic activity detectors.

22. The system of claim 15 further comprising an enable array accessible to the processor and further wherein the processor is adapted to control the therapy circuit based on a logical AND of the status array with the enable array.

23. The system of claim 15 further comprising a first in first out (FIFO) buffer coupled to the plurality of timers.

24. The system of claim 15 wherein the processor includes a microprocessor.

25. A method comprising:
   sensing a plurality of cardiac events;
   starting a plurality of timers based on a predetermined cardiac event of the plurality of cardiac events;
   for each timer of the plurality of timers, storing a timer status bit in a status array;
   for one or more of the plurality of cardiac events, storing a sense status bit in the status array;
   masking the status array to determine a mode; and
   executing a function based on the mode and the status array.

26. The method of claim 25 further comprising receiving the status array in a first in first out (FIFO) buffer.

27. The method of claim 25 wherein storing a sense status bit includes storing a bit corresponding to an intrinsic cardiac activity.

28. The method of claim 25 further comprising delivering an escape beat upon expiration of a particular timer of the plurality of timers.

29. The method of claim 25 further comprising allowing selected timers of the plurality of timers to expire.

30. The method of claim 25 further comprising executing computer implemented instructions adapted to perform the sensing, starting, storing the timer status bit, storing the sense status bit, masking and executing.

31. The method of claim 25 further comprising repeating the sensing, starting, storing the timer status bit, storing the sense status bit, masking and executing.

* * * * *